United States Patent [19]

Defossez et al.

[11] Patent Number: 5,486,354
[45] Date of Patent: Jan. 23, 1996

[54] COSMETIC MAKE-UP COMPOSITION CONTAINING A TRANSPARENT TITANIUM OXIDE AND SILICON OXIDE PIGMENT

[75] Inventors: Béatrice Defossez; Sylvie Rossignol, both of Paris, France

[73] Assignee: L'Oreal, Paris, France

[21] Appl. No.: 122,469

[22] PCT Filed: Jan. 29, 1993

[86] PCT No.: PCT/FR93/00099

§ 371 Date: Sep. 29, 1993

§ 102(e) Date: Sep. 29, 1993

[87] PCT Pub. No.: WO93/14739

PCT Pub. Date: Apr. 5, 1993

[30] Foreign Application Priority Data

Jan. 31, 1992 [FR] France .................................. 92 01086

[51] Int. Cl.$^6$ .............................. A61K 7/021; A61K 7/00
[52] U.S. Cl. .................. 424/63; 424/61; 424/69; 514/938
[58] Field of Search .................... 424/63, 61, 69; 514/938

[56] References Cited

U.S. PATENT DOCUMENTS

| | | | |
|---|---|---|---|
| 3,331,699 | 7/1967 | Marshall et al. | 424/63 |
| 5,169,442 | 12/1992 | Noguchi et al. | 424/63 |

FOREIGN PATENT DOCUMENTS

| | | | |
|---|---|---|---|
| 268938 | 6/1988 | European Pat. Off. | 424/59 |
| 377326 | 7/1990 | European Pat. Off. | 424/59 |
| 2226018 | 6/1990 | United Kingdom | 424/59 |

OTHER PUBLICATIONS

Matsuoka et al, "Manufacture of cosmetic aerosols containing silica–treated titanium oxide colloidal solutions", S.T.N. Chemical Abstracts, vol. 111, No. 180453, 1989.

*Primary Examiner*—C. Warren Ivy
*Assistant Examiner*—Zinna N. Davis
*Attorney, Agent, or Firm*—Cushman Darby & Cushman

[57] ABSTRACT

A cosmetic make-up composition containing, in a suitable cosmetic carrier, a transparent pigment consisting of at least 60 wt % laminar titanium oxide and at most 10 wt % silicon oxide, wherein the average pigment size is 1–300 μm and the thickness is 0.001–0.3 μm. Excellent cosmetic properties regarding pearlizing, coverage, spreadability and smoothness are obtained.

11 Claims, No Drawings

COSMETIC MAKE-UP COMPOSITION CONTAINING A TRANSPARENT TITANIUM OXIDE AND SILICON OXIDE PIGMENT

This application is a 371 of PCT/FR93/00099 filed Jan. 29, 1993.

The subject of the present invention is a cosmetic make-up composition, the latter containing a transparent titanium oxide and silicon oxide pigment.

Make-up products such as loose or compacted powders, foundations, blushers, eye shadows, lipsticks as well as nail varnishes contain, in variable proportions, pigments intended to confer on these products some color as well as optionally inorganic fillers intended especially to provide a good covering power.

In order to obtain a covering effect, titanium dioxide may be used as opacifying white pigment. However its use renders the spreading of the compositions on the skin difficult and brings about its whitening. If it is desired, in addition, to obtain a pearlescent effect, a pearlescent pigment such as titanium oxide-coated mica (mica-titanium) or bismuth oxychloride should be added. However, the use of mica-titanium can have disadvantages linked to poor spreading and to the lack of smoothness.

Furthermore, when it is desired to enhance the pearlescent effect, it is possible to increase the amount of mother-of-pearl but in this case, problems of cohesion are encountered which necessitate increasing the amount of binder such that it causes inconvenience during application. Finally, it should be noted that mother-of-pearls are particularly fragile particles which, when they are ground, lose their pearlescent effect.

If it is desired to confer a pronounced colored effect, it is necessary to use colored organic or inorganic pigments, but increasing the amount of pigments causes, on the one hand, a color saturation and, on the other hand, problems of homogeneity of the pigments in the formula.

If it is desired to enhance the colored effect of the pigments, iron oxide for example may be incorporated, as described in Patent Application JP 61-295234, into the lamellar titanium dioxide coating layer.

After various studies with a view to overcome the abovementioned disadvantages, it was observed, surprisingly, that by using, as pearling agent in a cosmetic make-up composition, a transparent pigment consisting of at least 60% by weight of titanium oxide and at most 10% by weight of silicon oxide, it was possible to obtain excellent cosmetic properties, these transparent pigments conferring at the same time a satisfactory pearliness and an appropriate level of coverage, a high spreadability and a smoothness which is not observed with conventional pearly pigments. A more homogeneous film is also obtained in which the transparent pigments are well distributed.

These transparent pigments, because of their shiny, pearly and colored iridescent effect, and by virtue of their cosmetic properties, are particularly suitable for a cosmetic use without the disadvantages of the pigments of the prior state of the art being encountered. Furthermore, these transparent pigments are less fragile than the mother-of-pearls, which makes it possible to grind them without losing their pearlescent effect.

The subject of the present invention is therefore a cosmetic make-up composition containing, in a suitable cosmetic carrier, a transparent pigment consisting of at least 60% by weight of titanium oxide in lamellar form and at most 10% by weight of silicon oxide, the mean size of the pigments being between 1 and 300 μm and the thickness between 0.001 to 0.3 μm.

Preferably, the transparent pigments consist of at least 90% by weight of titanium oxide, in lamellar form, and at most 6% by weight of silicon oxide.

According to a preferred embodiment of the invention, the mean size of the transparent pigments is between 5 and 50 μm, and the thickness between 0.01 and 0.2 μm and more particularly between 0.1 and 0.2 μm.

The transparent pigments of the cosmetic composition according to the invention are described in European Patent Application EP 377 326 to which reference is made herein. These transparent pigments are, according to this application, obtained by dissolution of a major part of the silicon oxide of silicon oxide particles coated with transparent titanium oxide, choosing silicon oxide particles for which a major part of the silicon oxide is soluble in a base such as sodium hydroxide or potassium hydroxide.

As transparent titanium oxide and silicon oxide pigments, there may be used those sold by the company KEMIRA under the names FLONAC "TS40C®", "TS50C®", "TS60C®" and "TS70C®".

The product "TS40C®" consists of 94% titanium oxide and 4% silicon oxide and is provided in the form of a crystalline powder exhibiting red shimmers.

The product "TS50C®" consists of 94% titanium oxide and 4% silicon oxide and is provided in the form of a crystalline powder exhibiting lilac shimmers.

The product "TS60C®" consists of 94% titanium oxide and 4% silicon oxide and is provided in the form of a crystalline powder exhibiting blue shimmers.

The product "TS70C®" consists of 94% titanium oxide and 4% silicon oxide and is provided in the form of a crystalline powder exhibiting green shimmers.

In the make-up products according to the invention, the transparent pigment as defined above is generally present at a concentration of between 0.5 and 30% and preferably between 0.5 and 10% by weight relative to the total weight of the composition.

The cosmetic compositions according to the invention can be used as make-up products for the skin, the eyes or the hair.

When the cosmetic compositions are intended as make-up for the skin, they are essentially eye shadows, eye liners, mascaras, powders, foundations, blushers, colored creams, lipsticks or cover sticks.

The transparent pigments also find application in nail varnishes.

Preferably, the cosmetic compositions according to the invention are more particularly intended as eye make-up, that is to say in the form of eye shadows, eye liners or mascaras.

The cosmetic make-up compositions according to the invention may, in addition, contain other pigments and/or additional fillers which are common in cosmetics.

Among the inorganic pigments, there may be mentioned the metallic oxides obtained by the synthetic route or of natural origin such as iron, titanium, zinc or chromium oxide and the like, and by way of examples:

titanium dioxide (rutile or anatase) optionally treated superficially and coded in the Colour Index under the reference CI 77891;

black iron, yellow, red and brown oxides, coded under the references CI 77499, 77492, 77491;

magnesium violet (CI 77742);

ultramarine blue (CI 77007);

hydrated chromium oxide (CI 77289);

ferrite blue (CI 77510);

and all the inorganic pigments having undergone an inorganic or organic surface treatment.

Among the organic pigments, the following may be mentioned in particular:

| | |
|---|---|
| D & C red No. 19 | (CI 45170); |
| D & C red No. 9 | (CI 15585); |
| D & C red No. 21 | (CI 45380); |
| D & C orange No. 4 | (CI 15510); |
| D & C orange No. 5 | (CI 45370); |
| D & C red No. 27 | (CI 45410); |
| D & C red No. 13 | (CI 15630); |
| D & C red No. 7 | (CI 15850-1); |
| D & C red No. 6 | (CI 15850-2); |
| D & C yellow No. 5 | (CI 19140); |
| D & C red No. 36 | (CI 12085); |
| D & C orange No. 10 | (CI 45425); |
| D & C yellow No. 6 | (CI 15985); |
| D & C red No. 30 | (CI 73360); |
| D & C red No. 3 | (CI 45430); |
| carbon black | (CI 77266); and |
| lacquers based on cochineal carmine (CI 75470). | |

According to the invention, the additional pigments may represent from 0.01 to 30% by weight of the composition, preferably from 0.2 to 15%.

The fillers are chosen especially from:

silica, sericite, talc, which is a hydrated magnesium silicate used in the form of particles generally less than 40 µm in size; the talc possesses moisture-absorbing properties and is used especially because of its unctuous feel;

micas, which are aluminosilicates of varying compositions, which exist in the form of scales of 2 to 200 µm, preferably 5 to 70 µm in size and having a thickness of 0.1 to 5 µm, preferably 0.2 to 3 µm. Micas may be of natural origin (for example muscovite, margarite, roscoelite, lepidolite and biotite) or of synthetic origin. The micas are generally transparent and make it possible to confer a satiny appearance on the skin;

starch, in particular rice starch;

kaolin, which is a hydrated aluminum silicate, which exists in the form of particles of isotropic shape generally less than 30 µm in size, and which possesses good fat-absorbing properties;

zinc and titanium oxides, which are generally used in the form of particles not exceeding a few micrometres in size (or even less than 1 µm in the case of titanium oxide): these oxides have an unctuous feel, a good covering power and a high opacity;

boron nitride;

precipitated calcium carbonate which, in the form of particles less than 10 µm in size, has an unctuous feel and makes it possible to obtain a matt appearance;

magnesium carbonate or hydrocarbonate, which possess especially perfume fixing properties;

metallic soaps derived from organic carboxylic acids having 8 to 22 carbon atoms, preferably 12 to 18 carbon atoms, for example zinc, magnesium or lithium stearate, zinc laurate, magnesium myristate and the like. These soaps, which are generally present in the form of particles less than 10 µm in size, have an unctuous feel and facilitate the adhesion of the powder onto the skin;

powders based on synthetic polymers such as polyethylene, polyesters (for example polyethylene isophthalate or terephthalate), polyamides, in the form of particles less than 50 µm in size, which possess absorbent properties, and make it possible to confer a velvety appearance on the skin, methacrylate powders;

hollow microspheres, such as for example the hollow microspheres XPANCEL® sold by the company Kemanord Plast AB and described in French Patent 86 09289 (2,600,532).

According to the invention, the additional fillers may represent from 0.01 to 90% by weight of the composition.

The compositions according to the present invention may be provided especially in the form of an oil-in-water or water-in-oil emulsion, or in the form of a suspension in solvent medium, or alternatively in the form of a loose powder, compacted powder or anhydrous paste. The procedures for the preparation of these various types of compositions are well known to persons skilled in the art.

When they are used in the form of an emulsion, the compositions may contain surface-active agents which are well known in the state of the art. These surface-active agents may constitute from 0.01 to 30% by weight of the composition.

A particularly preferred embodiment consists in preparing anionic or non-ionic emulsions using anionic or non-ionic surface-active agents such as those listed in French Patent Application No. 2,629,713, in proportions preferably of between 2 and 30% by weight relative to the total weight of the composition.

In these emulsions, the oily phase may represent from 0.1 to 50% by weight of the emulsion. It may consist of oils and/or waxes well known in the state of the art. The waxes and oils may be of plant, animal, inorganic or synthetic origins.

The oily phase may furthermore contain colorants, sunscreen agents, anti-oxidants, preservatives and lipophilic active ingredients.

When the emulsion contains a sunscreen agent, especially in proportions ranging from 0.5 to 15% by weight relative to the total weight of the composition, the above defined transparent pigments provide an aesthetic appearance to the screening composition.

The compositions conforming to the present invention may contain, in addition to the components mentioned above, conventional ingredients used especially in make-up compositions and chosen from emollients, preservatives, sequestrants, perfumes, thickeners, cohesion agents, polymers as well as the alkalinising or acidifying agents normally used in the cosmetic field, and moisturizers.

The thickeners which can be used may be natural or synthetic. Among the natural thickeners, there may be mentioned various gums such as gum arabic, guar gum or carob gum. Among the synthetic thickeners, there may be mentioned cellulose derivatives such as hydroxyethylcellulose, carboxymethylcellulose, starch derivatives, cellulose ether derivatives possessing quaternary ammonium groups, cationic polysaccharides and salts of acrylic or methacrylic polymers.

A thickener for the compositions can also be obtained by mixing polyethylene glycol and polyethylene glycol stearate and/or distearate or by the mixing of phosphoric esters and fatty amides.

These thickeners are especially used as pigment-suspending agents and facilitate the homogeneous distribution of the pigment in the composition. They are therefore suitable for compositions provided in the form of a suspension for the temporary dyeing of keratinous fibres, in particular hair, which are removable with the first shampooing.

According to the invention, the anhydrous compositions which may be provided in the form of loose or compacted powder, solid, pasty or liquid blusher may contain a binder which may preferably represent from 0.01 to 95% by weight.

Among the binding agents, there may be mentioned especially animal, vegetable or synthetic oils, mixtures of oil(s) and wax(es), and in particular vison oil, tortoise oil, soya bean oil, grape seed oil, sesame oil, maize oil, colza oil, sunflower oil, cotton seed oil, avocado oil, olive oil, castor oil, jojoba oil, groundnut oil and the like; hydrocarbon oils such as paraffin oils, squalane, vaseline, and the like; esters such as isopropyl myristate, isopropyl palmitate, butyl stearate, hexyl laurate, isononyl isononanate, 2-ethylhexyl palmitate, 2-hexyldecyl laurate, 2-octyldecyl palmitate, 2-octyldodecyl myristate, 2-diethylhexyl succinate, diisostearyle malate, 2-octyldodecyl lactate, glycerin triisostearate, diglycerin triisostearate and the like; silicone oils such as polymethylsiloxanes, polymethylphenylsiloxanes, polysiloxanes modified by fatty acids, polysiloxanes modified by fatty alcohols, polysiloxanes modified by polyoxyalkylenes, fluorinated silicones and the like; fluorinated and/or organofluorinated oils; higher fatty acids such as myristic acid, palmitic acid, stearic acid, behenic acid, oleic acid, linoleic acid, linolenic acid, isostearic acid, and the like; higher fatty alcohols such as cetanol, stearyl alcohol, oleyl alcohol and the like; the waxes may be chosen especially from carnauba wax, candelilla wax, beeswax, whale wax, lanolins, microcrystalline waxes and the like.

The binder may contain, in addition, volatile oils which evaporate upon contact with the skin, but whose presence, in the cosmetic composition, is useful because they facilitate the spreading of the composition during appplication to the skin. Such spreading agents, here called "volatile oils", are generally oils having, at 25° C., a saturation vapor pressure at least equal to 0.5 millibar (equivalent to $0.5 \times 10^2$ Pa).

Among the volatile oils which may be present as spreading agents in the composition of the invention, there may be mentioned for example silicone oils such as hexamethyldisiloxane, cyclopentadimethylsiloxane, cyclotetramethylsiloxane, fluorinated oils such as that marketed under the name GALDEN (MONTEFLUOS) or isoparaffin oils such as those marketed under the name ISOPAR (E, G, L or H)®.

As mentioned above, the compositions according to the invention may also be provided in the form of a nail varnish containing the transparent pigment in a proportion of 0.01 to 10% by weight.

The solvent system for the varnish generally represents from 55 to 90% by weight of the total weight of the varnish.

This solvent system consists of a mixture of various volatile organic solvents such as acetone, ethyl acetate, butyl acetate, 2-methoxyethyl acetate, methyl ethyl ketone, methyl isobutyl ketone, methyl acetate, amyl acetate and isopropyl acetate.

The solvent system may generally comprise a diluent such as hexane or octane or alternatively an aromatic hydrocarbon such as toluene or xylene in a proportion of 10 to 35% by weight relative to the total weight of the varnish.

The film-forming material of the varnish is generally present at a concentration of between 5 and 20% by weight relative to the total weight of the varnish.

Among the film-forming materials, there may be mentioned especially the "RS" or "SS" type nitrocelluloses and in particular the ¼"RS" type nitrocellulose, ½"RS" type nitrocellulose, ½"SS" type nitrocellulose and ¾"RS" type nitrocellulose.

The varnishes also contain a plasticizing agent which is generally present at a concentration of between 2 and 10% by weight relative to the total weight of the varnish. Among them, there may be mentioned especially tricresyl phosphate, benzyl benzoate, triethyl citrate, tributyl citrate, triethyl acetylcitrate, 2-triethylhexyl acetylcitrate, diamyl phthalate and camphor.

The varnishes according to the invention also contain a resin which is generally present at a concentration of between 0.5 and 15% by weight relative to the total weight of the varnish.

Among the numerous resins which can be used, there may be mentioned especially aryl-sulphonamide formaldehyde or aryl-sulphonamide epoxy type resins especially the resins known under the commercial names "SANTOLITE MHP®" and "SANTOLITE MS 80%®".

The nail varnishes according to the invention may also contain adjuvants routinely used in nail varnishes such as for example UV-screening agents.

Several examples of cosmetic make-up compositions according to the invention will now be given by way of illustration and with no limitation being implied.

Example 1: eye shadow

| | |
|---|---|
| Mica | 10.0 g |
| Nylon powders sold under the name "ORGASOL ®" by the company Atochem | 15.0 g |
| Zinc stearate | 3.0 g |
| Red iron oxide | 0.5 g |
| Yellow iron oxide | 2.0 g |
| Titanium oxide and silica pigment sold under the name FLONAC R "TS40 ®" by the company KEMIRA | 5.0 g |
| Vaseline oil | 3.0 g |
| Vaseline | 0.6 g |
| Lanolin | 0.6 g |
| Castor oil | 1.8 g |
| Talc qs. | 100 g |

For comparison, the same formula is reproduced replacing the FLONAC R "TS40"® pigment with mica-titanium.

The composition according to the invention is superior to that obtained with the mica-titanium from the point of view of ease of spreading, homogeneity, smoothness and coverage.

Example 2: eye shadow

| | |
|---|---|
| Mica | 20.0 g |
| Zinc stearate | 3.0 g |
| Black iron oxide | 0.5 g |
| Yellow iron oxide | 2.0 g |
| Titanium oxide and silica pigment sold under the name FLONAC R "TS70C ®" by the company KEMIRA | 5.0 g |
| Vaseline oil | 5.4 g |
| Oleyl alcohol | 1.0 g |
| Vaseline | 1.0 g |
| Isopropyl myristate | 0.8 g |
| Propyl para-hydroxybenzoate | 0.2 g |
| Talc qs. | 100 g |

For comparison, the same formula was reproduced replacing the FLONAC R "TS70C®" pigment with bismuth oxychloride.

The composition according to the invention exhibits a superior cohesion and from the make-up point of view, there is an iridescent colored effect which is not obtained in the presence of bismuth oxychloride.

Example 3: blusher

| | |
|---|---|
| Microspheres of cross-linked poly-β-alanine impregnated with 300% g | 4.0 g |

| | |
|---|---|
| glycerol | |
| Petrolatum sold under the name "SERAFINE 56/58 ®" by the company SERESINE | 10.0 g |
| Carnauba wax | 5.0 g |
| Polyethylene wax | 5.0 g |
| Titanium oxide and silica pigment sold under the name FLONAC R "TS40C ®" by the company KEMIRA | 10.0 g |
| Titanium dioxide | 5.0 g |
| D & C red no. 7 sold under the name "W005 ®" by the company WACKHERR | 0.2 g |
| Black iron oxide qs | |
| Yellow iron oxide qs | |
| Red iron oxide qs | |
| Propyl para-hydroxybenzoate | 0.1 g |
| Butylated hydroxytoluene | 0.05 g |
| Paraffin oil sold under the name "MARCOL 82 ®" by the company ESSO qs. | 100 g |

Example 4: colored nail varnish

| | |
|---|---|
| Nitrocellulose | 10.62 g |
| Toluene sulphonamide formaldehyde resin sold under the name "KETJENFLEX MS80 ®" by the company AKZO | 9.54 g |
| Tributyl acetylcitrate sold under the name "CITROFLEX A4 ®" by the company PFIZER | 6.32 g |
| Toluene | 30.28 g |
| Butyl acetate | 21.13 g |
| Ethyl acetate | 9.15 g |
| Isopropyl alcohol | 7.60 g |
| Stearalkonium hectorre sold under the name "BENTONE 27 ®" by the company NL CHEMICALS | 1.35 g |
| Pigments | 1.0 g |
| Titanium oxide and silica pigment sold under the name FLONAC R "TS40C ®" by the company KEMIRA | 1.0 g |
| Citric acid | 0.06 g |

Example 5: foundation

| | |
|---|---|
| Glycerol stearate | 2.2 g |
| Triglycerides of capric/caprylic acids sold under the name "MIGLYOL 812 ®" by the company DYNAMIT NOBEL | 15.0 g |
| Yellow iron oxides | 0.75 g |
| Brown iron oxides | 0.47 g |
| Black iron oxide | 0.23 g |
| Titanium dioxide | 4.55 g |
| Methyl para-hydroxybenzoate | 0.1 g |
| Propyl para-hydroxybenzoate | 0.1 g |
| Imidazolidinyl urea | 0.3 g |
| 2-hydroxy-4-methoxybenzophenone | 0.5 g |
| Octyl N,N-dimethylparaaminobenzoate. | 0.5 g |
| Titanium oxide and silica pigment sold under the name FLONAC R "TS40C ®" by the company KEMIRA | 3.0 g |
| Aluminum and magnesium silicate sold under the name "VEEGUM ®" by the company VENDERBILT | 1.0 g |
| Triethanolamine | 1.0 g |
| Cellulose gum | 0.16 g |
| Aluminium salt of the product of the reaction of octenylsuccinic anhydride with starch sold under the name "DRY FLO ®" a by the company NATIONAL STARCH | 5.0 g |
| Cyclomethicone sold under the name "VOLATIL SILICONE 7158 ®" by the company UNION CARBIDE | 10.0 g |
| Water | 47.34 g |
| Propylene glycol | 2.0 g |
| Glycerin | 3.0 g |
| Sodium salt of lauroylsarcosine sold under the name "ORAMIX L30 ®" by the company SEPPIC | 0.6 g |
| Stearic acid | 2.2 g |

Example 6: foundation

| | |
|---|---|
| Glycerol stearate | 2.2 g |
| Triglycerides of capric/caprylic acids sold under the name "MIGLYOL 812 ®" by the company DYNAMIT NOBEL | 15.0 g |
| Yellow iron oxides | 0.75 g |
| Brown iron oxides | 0.47 g |
| Black iron oxide | 0.23 g |
| Titanium dioxide | 4.55 g |
| Methyl para-hydroxybenzoate | 0.1 g |
| Propyl para-hydroxybenzoate | 0.1 g |
| Imidazolidinyl urea | 0.3 g |
| 2-hydroxy-4-methoxybenzophenone | 0.5 g |
| Octyl N,N-dimethylparaaminobenzoate. | 0.5 g |
| Titanium oxide and silica pigment sold under the name FLONAC R "TS70C ®" by the company KEMIRA | 3.0 g |
| Aluminum and magnesiut silicate sold under the name "VEEGUM ®" by the company VENDERBILT | 1.0 g |
| Triethanolamine | 1.0 g |
| Cellulose gum | 0.16 g |
| Aluminum salt of the product of the reaction of octenylsuccinic anhydride with starch sold under the name "DRY FLO ®" by the company NATIONAL STARCH | 5.0 g |
| Cyclomethicone sold under the name "VOLATIL SILICONE 7158 ®" by the company UNION CARBIDE | 10.0 g |
| Water | 47.34 g |
| Propylene glycol | 2.0 g |
| Glycerin | 3.0 g |
| Sodium salt of lauroylsarcosine sold under the name "ORAMIX L30 ®" by the company SEPPIC | 0.6 g |
| Stearic acid | 2.2 g |

Example 7: eye shadow

| | |
|---|---|
| Iron oxide | 10.7 g |
| D & C red no. 30 | 0.02 g |
| Mica | 20 g |
| Bismuth oxychloride | 14 g |
| Nylon powder sold under the name "ORGASOL ®" by the company ATOCHEM | 15 g |
| Zinc stearate | 3 g |
| Titanium oxide and silica pigment sold under the name FLONAC R "TS60C ®" by the company KEMIRA | 10 g |
| Vaseline | 0.7 g |
| Vaseline oil | 3.8 g |
| Lanolin | 0.39 g |
| Castor oil | 0.76 g |
| Propyl para-hydroxybenzoate | 0.14 g |
| Talc qs. | 100 g |

This composition provides an iridescent pearlescent effect and an appropriate level of coverage.

Example 8: blusher

| | |
|---|---|
| Zinc stearate | 3 g |
| Titanium oxide | 2 g |
| Iron oxide | 9 g |
| Mica | 24 g |
| Nylon powder sold under the name | 15 g |

-continued

| | |
|---|---|
| ORGASO ® by the company ATOCHEM | |
| Titanium oxide and silica pigment | 5 g |
| sold under the name FLONAC R "TS40C ®" | |
| by the company KEMIRA | |
| Vaseline oil | 3.26 g |
| Oleyl alcohol | 0.6 g |
| Isopropyl myristate | 0.43 g |
| Propyl para-hydroxybenzoate | 0.12 g |
| Talc qs. | 100 g |

By comparison, the same formula is reproduced without the FLONAC R TS40C® pigment.

The composition according to the invention provides an iridescent colored effect and a highly smooth feel.

Example 9: loose face powder

| | |
|---|---|
| Iron oxide | 0.5 g |
| Zinc stearate | 2 g |
| Zinc oxide | 2 g |
| Kaolin | 2 g |
| Nylon powder sold under the name "ORGASOL ®" by the company ATOCHEM | 30 g |
| Vaseline oil | 4 g |
| Titanium oxide and silica pigment sold under the name FLONAC R "TS40C ®" by the company KEMIRA | 3 g |
| Talc qs | 100 g |

Example 10: compacted face powder

| | |
|---|---|
| Iron oxide | 6.57 g |
| Zinc stearate | 4 g |
| Titanium dioxide | 2 g |
| Bismuth oxychloride | 10 g |
| Nylon powder sold under the name "ORGASOL ®" by the company ATOCHEM | 20 g |
| Vaseline oil | 3.26 g |
| Oleyl alcohol | 0.6 g |
| Isopropyl myristate | 0.43 g |
| Propyl para-hydroxybenzoate | 0.12 g |
| Titanium oxide and silica pigment sold under the name FLONAC R "TS40C ®" by the company KEMIRA | 5 g |
| Talc qs. | 100 g |

We claim:

1. A cosmetic make-up composition comprising, in a cosmetic carrier, 0.5 to 30 percent by weight, relative to the total weight of said composition, of a transparent pigment comprising at least 60 percent by weight of titanium oxide in lamellar form and at most 10 percent by weight of silicon oxide, said transparent pigment having a mean size ranging from 1 to 300 μm and a thickness ranging from 0.001 to 0.3 μm.

2. The cosmetic make-up composition of claim 1 wherein said transparent pigment comprises at least 90 percent by weight of titanium oxide and at most 6 percent by weight of silicon oxide.

3. The cosmetic make-up composition of claim 1 wherein said transparent pigment comprises about 94 percent by weight of titanium oxide and 4 percent by weight of silicon oxide.

4. The cosmetic make-up composition of claim 1 wherein said mean size of said transparent pigment ranges from 5 to 50 μm and said thickness ranges from 0.01 to 0.2 μm.

5. The cosmetic make-up composition of claim 1 wherein said transparent pigment is present in an amount ranging from 0.5 to 10 percent by weight relative to the total weight of said composition.

6. The cosmetic make-up composition of claim 1 which also contains at least one additional filler present in an amount ranging from 0.01 to 90 percent by weight relative to the total weight of said composition.

7. The cosmetic make-up composition of claim 1 wherein said cosmetic carrier is selected from the group consisting of an oil-in-water emulsion, a water-in-oil emulsion, a suspension, a loose powder, a compacted powder, a solid paste, an anhydrous paste and a nail varnish.

8. The cosmetic make-up composition of claim 7 wherein said oil-in-water emulsion or said water-in-oil emulsion contains a surface-active agent present in an amount ranging from 0.01 to 30 percent by weight of said composition.

9. The cosmetic make-up composition of claim 7 wherein said solid paste or said anhydrous paste contains at least one binding agent present in an amount ranging from 0.01 to 95 percent by weight relative to the total weight of said composition.

10. The cosmetic make-up composition of claim 7 wherein said nail varnish contains 55 to 90 percent by weight of a solvent system, 5 to 20 percent by weight of a film-forming material, 2 to 10 percent by weight of a plasticizing agent and 0.5 to 15 percent by weight of a resin.

11. The cosmetic make-up composition of claim 10 wherein said nail varnish contains from 0.01 to 10 percent by weight of said transparent pigment.

* * * * *

UNITED STATES PATENT AND TRADEMARK OFFICE
CERTIFICATE OF CORRECTION

PATENT NO. : 5,486,354

DATED : January 23, 1996

INVENTOR(S) : DEFOSSEZ ET AL

It is certified that error appears in the above-indentified patent and that said Letters Patent is hereby corrected as shown below:

On the Title page, item [86]
change the 102(e) Date to --Jan. 07, 1994--.

Signed and Sealed this

Fourteenth Day of May, 1996

Attest:

BRUCE LEHMAN

*Attesting Officer*     *Commissioner of Patents and Trademarks*